United States Patent
Nguyen et al.

(10) Patent No.: US 12,077,560 B2
(45) Date of Patent: Sep. 3, 2024

(54) DEVICES AND METHODS FOR THE SENSITIVE DETECTION AND QUANTITATION OF BIOMOLECULES

(71) Applicant: Waters Technologies Corporation, Milford, MA (US)

(72) Inventors: Jennifer M. Nguyen, Uxbridge, MA (US); Matthew A. Lauber, North Smithfield, RI (US); Yun Wang Alelyunas, Stow, MA (US); Gregory T. Roman, North Scituate, RI (US); Henry Y. Shion, Hopkinton, MA (US)

(73) Assignee: Waters Technologies Corporation, Milford, MA (US)

( * ) Notice: Subject to any disclaimer, the term of this patent is extended or adjusted under 35 U.S.C. 154(b) by 766 days.

(21) Appl. No.: 17/211,092

(22) Filed: Mar. 24, 2021

(65) Prior Publication Data
US 2021/0300965 A1  Sep. 30, 2021

Related U.S. Application Data

(60) Provisional application No. 62/994,431, filed on Mar. 25, 2020.

(51) Int. Cl.
| | |
|---|---|
| *B01L 3/00* | (2006.01) |
| *A23C 9/146* | (2006.01) |
| *B01D 53/10* | (2006.01) |
| *B01F 23/00* | (2022.01) |
| *B01F 23/41* | (2022.01) |

(Continued)

(52) U.S. Cl.
CPC ............... *C07K 1/18* (2013.01); *B01D 53/10* (2013.01); *A23C 9/1465* (2013.01); *C12Q 2547/101* (2013.01)

(58) Field of Classification Search
CPC .......... B01L 3/502753; B01L 3/50273; B01L 2200/0621; B01L 2300/0681; B01L 2300/0816; B01L 2400/0481; B01L 2400/0633; B01L 2300/0867; B01L 2300/0887
See application file for complete search history.

(56) References Cited

U.S. PATENT DOCUMENTS

| | | | |
|---|---|---|---|
| 8,383,340 B2 | 2/2013 | Ketterer et al. | |
| 2003/0130172 A1* | 7/2003 | Belvo ................. | C07K 9/008 530/322 |

(Continued)

FOREIGN PATENT DOCUMENTS

WO  WO-2016100447 A1 *  6/2016  ......... B01D 15/3847

OTHER PUBLICATIONS

Chen, Michelle Hong, and Csaba Horváth. "Temperature programming and gradient elution in reversed-phase chromatography with packed capillary columns." Journal of Chromatography A 788.1-2 (1997): 51-61. (Year: 1997).*

(Continued)

*Primary Examiner* — Jennifer Wecker
*Assistant Examiner* — Oyeleye Alexander Alabi
(74) *Attorney, Agent, or Firm* — WOMBLE BOND DICKINSON (US) LLP; Deborah M. Vernon; Ricardo Joseph (57) ABSTRACT

The present disclosure provides devices, systems, kits and methods useful for quantitation of biomolecules such as intact proteins and nucleic acids.

13 Claims, 7 Drawing Sheets

(51) Int. Cl.
    B01F 101/23    (2022.01)
    B23Q 17/24    (2006.01)
    C07K 1/18    (2006.01)
    C12M 1/34    (2006.01)
    C12Q 1/04    (2006.01)
    C12Q 1/18    (2006.01)
    G01N 21/3577    (2014.01)
    G01N 21/359    (2014.01)
    G01N 21/39    (2006.01)
    G01N 21/45    (2006.01)
    G01N 21/64    (2006.01)
    G01N 30/12    (2006.01)
    G01N 30/68    (2006.01)
    G01N 30/70    (2006.01)
    G01N 30/72    (2006.01)
    G01N 30/88    (2006.01)
    G01N 33/00    (2006.01)
    G01N 33/18    (2006.01)
    G01N 33/50    (2006.01)
    G01N 33/68    (2006.01)

(56)  References Cited

U.S. PATENT DOCUMENTS

| | | | | |
|---|---|---|---|---|
| 2005/0161399 A1* | 7/2005 | Dillon | ............. | G01N 30/30 |
| | | | | 436/171 |
| 2010/0048883 A1* | 2/2010 | Ketterer | ............. | C12N 15/101 |
| | | | | 536/25.41 |
| 2015/0204824 A1* | 7/2015 | Lauber | ............. | B01J 20/3272 |
| | | | | 210/502.1 |
| 2017/0082606 A1* | 3/2017 | Caprioli | ............. | G01N 33/573 |
| 2017/0246223 A1* | 8/2017 | Tangney | ............. | A61K 31/165 |
| 2019/0317062 A1 | 10/2019 | Fogwill et al. | | |

OTHER PUBLICATIONS

Fekete, Szabolcs, et al. "Proof of concept to achieve infinite selectivity for the chromatographic separation of therapeutic proteins." Analytical chemistry 91.20 (2019): 12954-12961. (Year: 2019).*

Lopez, Mary F., et al. "Selected-Reaction Monitoring-Mass Spectrometric Immunoassay Analysis of Parathyroid Hormone and Related Variants." (Year: 2017).*

Allen, Darren R., and Brett C. McWhinney. "Quadrupole time-of-flight mass spectrometry: a paradigm shift in toxicology screening applications." The Clinical Biochemist Reviews 40.3 (2019): 135. (Year: 2019).*

ThermoFisher (MAbPac RP Columns) chrome-extension://efaidnbmnnnibpcajpcglclefindmkaj/https://assets.thermofisher.com/TFS-Assets/CMD/manuals/Man-065625-LC-MAbPac-RP-cols. Man065625-EN.pdf (Year: 2017).*

International Search Report and Written Opinion for International application No. PCT/US2021/023887, mailed on Jul. 1, 2021, 12 pages.

Fekete, et al., "Proof of concept to achieve infinite selectivity for the chromatographic separation of therapeutic proteins", Anal. Chem. 91, 12954-12961(2019) Abstract.

Ferrige, A.G., et al., "Disentangling electrospray spectra with maximum entropy", Rapid Comm. Mass Spectrom, 6 (11), 707-711 (1992) Abstract.

Ferrige, A.G., et al., "Maximum entropy deconvolution in electrospray mass spectrometry", Rapid Comm. Mass Spectrom 5 (8), 374-377 (1991) Abstract.

Maa, Y-F., et al., "Rapid analysis of proteins and peptides by reversed-phase chromatography with polymeric micropellicular sorbents", Journal of Chromatography A, 445:71-86 (1988). Abstract.

Murisier, A., et al., "Practical considerations on the particle size and permeability of ion-exchange columns applied to biopharmaceutical separations", J. Chromatogr. A. 1604, 1-10 (2019) Abstract.

Vasicek, L.A., et al., "Direct quantitation of therapeutic antibodies for pharmacokinetic studies using immune-purification and intact mass analysis", Bioanalysis 11 (03), 203-213 (2019) Abstract.

Wang, S., et al., "Simple approach for improved LC-MS analysis of protein biopharrnaceuticals via modification of desolvalion gas", Anal. Chem. 91, 3156-3162 (2019).

Weikart, C.M., et al., "Plasma-Treated Microplates with Enhanced Protein Recoveries and Minimized Extractables", SLAS Technology 22(1):98-105 (2017).

* cited by examiner

DEVICES AND METHODS FOR THE SENSITIVE DETECTION AND QUANTITATION OF BIOMOLECULES

CROSS-REFERENCE TO RELATED APPLICATIONS

This application claims the benefit of and priority to U.S. Provisional Patent Application No. 62/994,431, filed on Mar. 25, 2020, the entire contents of which is hereby incorporated by reference.

FIELD

The present disclosure provides devices, systems, kits and methods useful for quantitation of biomolecules such as intact proteins and nucleic acids.

BACKGROUND

Quantitative protein bioanalysis is typically performed by ligand binding assays (LBAs) or a bottom-up, surrogate peptide approach for liquid chromatography (LC)-mass spectrometry (MS) analysis. These two methods can often be used in complementary ways. However, because the target molecule becomes bound with epitopes and does not provide structural information (LBAs) or digested into small fragments (bottom-up LC-MS), the metabolic transformation of the molecule cannot be determined.

To address this need, an analyst can instead detect and quantify intact proteins with MS detection. Recent technological advances in high resolution mass spectrometry (HRMS) coupled with improvements in sample preparation have led to the use of reversed phase liquid chromatography (RPLC) for the bioanalysis of intact proteins. Unlike alternative methods, RPLC-HRMS on intact proteins can provide a more complete picture on what exactly is being quantified in any given assay. Additionally, since there is no or only limited amounts of digestion used in the associated approaches, sample preparation times can be reduced. However, emerging attempts at this mode of analysis have shown that without proper optimization of both the LC and MS dimensions, intact protein quantitation can be quite challenging.

SUMMARY

The present disclosure provides devices, systems, kits and methods that address the challenges associated with biomolecule quantitation, including intact protein quantitation, where it is difficult to achieve good resolution and high protein recovery without loss to the stationary phase (i.e., sorbent particles) or column hardware, by employing a short column device with optimized stationary and mobile phases. This disclosure also addresses the issue of long run times being detrimental to high throughput, intact mass analysis. This disclosure further provides useful LC and MS methods for gaining mass spectrometric sensitivity to further improve detection.

In various aspects, the present disclosure provided chromatographic systems that comprise chromatographic separation devices that comprise (a) sorbent particles having width ranging from 0.5 to 100 μm and (b) a housing comprising an inlet, an outlet and an internal volume between the inlet and the outlet, the internal volume (i) being filled with a volume of the sorbent particles that has a length ranging from 5 to 50 mm and a width ranging from 50 μm to 10 mm or (ii) being configured to be filled with a volume of the sorbent particles that has a length ranging from 5 to 50 mm and a width ranging from 50 μm to 10 mm, wherein a direction of fluid flow from the inlet to the outlet of the housing is along the length of the volume of the sorbent particles. The volume of the sorbent particles is also referred to herein as a bed volume.

In various embodiments, which can be used in conjunction with the above aspects, the ratio of the length to the width of the volume of the sorbent particles ranges from 10:1 to 2:1. beneficially from 8:1 to 2:1.

In various embodiments, which can be used in conjunction with the above aspects and embodiments, the sorbent particles are porous particles, for example, comprising pore diameters ranging from 10 Å to 5000 Å, for example, ranging anywhere from 10 Å to 25 Å to 50 Å to 100 Å to 250 Å to 500 Å to 1000 Å to 2500 Å to 5000 Å (in other words, ranging between any two of the preceding values).

In various embodiments, which can be used in conjunction with any of the above aspects, sorbent particles are non-porous particles. In various embodiments, which can be used in conjunction with any of the above aspects and embodiments, the sorbent particles are spherical particles.

In various embodiments, which can be used in conjunction with any of the above aspects and embodiments, the sorbent particles range from 1.5 to 5 μm in width.

In various embodiments, which can be used in conjunction with any of the above aspects and embodiments, the volume of the sorbent particles has a length ranging from 5 to 20 mm.

In various embodiments, which can be used in conjunction with any of the above aspects and embodiments, the volume of the sorbent particles has a width ranging from 1 to 5 mm.

In various embodiments, which can be used in conjunction with any of the above aspects and embodiments, the volume of the sorbent particles is a cylindrical volume (in which case the width of the volume of the sorbent particles corresponds to the diameter of the cylindrical volume).

In various embodiments, which can be used in conjunction with any of the above aspects and embodiments, the sorbent particles comprise an organic polymer. In some of these embodiments, the organic polymer comprises at least one hydrophobic organic monomer. Specific examples of hydrophobic monomers include, for example, monofunctional and multifunctional aromatic monomers such as styrene and divinylbenzene, monofunctional and multifunctional olefin monomers such as ethylene, propylene or butylene, polycarbonate monomers, ethylene terephthalate, monofunctional and multifunctional fluorinated monomers such as fluoroethylene, 1,1-difluoroethylene), tetrafluoroethylene, chlorotrifluoroethylene, hexafluoropropylene, perfluoropropylvinylether, or perfluoromethylvinylether, monofunctional or multifunctional acrylate monomers, monofunctional or multifunctional methacrylate monomers, or any combination thereof, among others. In particular embodiments, the organic polymer comprises methyl methacrylate, styrene, divinyl benzene or any combination thereof, with a copolymer of styrene and divinyl benzene being preferred in some embodiments.

In various embodiments, which can be used in conjunction with any of the above aspects and embodiments, the housing is a chromatography column.

In various embodiments, which can be used in conjunction with any of the above aspects and embodiments, an internal surface of the housing surrounding the volume of the sorbent particles has a water contact angle of less than 60°.

In various embodiments, which can be used in conjunction with any of the above aspects and embodiments, the housing surrounding the volume of the sorbent particles is surrounded by a vacuum jacket or a heating unit. Examples of such housings, including vacuum-jacketed columns and heated columns, are described in United States Patent Application No. 2019/0317062 to Fogwill et al., which is hereby incorporated by reference.

For example, in some of these embodiments, a column may include an insulating member and/or a jacket. In various embodiments, the insulating member may be formed from a vacuum chamber surrounding the column. In some embodiments, the insulating member may include a vacuum chamber having a gas arranged therein. In some embodiments, the gas may be any of helium, hydrogen, neon, nitrogen, oxygen, carbon dioxide, argon, sulfur hexafluoride, krypton, and xenon. In some embodiments, the vacuum chamber may comprise atmospheric gas. In some embodiments, the column and insulating member may be integrated into a single component forming an insulated chromatography column. For example, a jacket may surround the column and the vacuum chamber may be formed in an area between the column and the jacket. In some embodiments, the jacket may be made of steel. The vacuum chamber forming the insulating member may provide thermal insulation for the column. The insulating member may substantially prevent a radial thermal gradient from forming within the column.

In some of these embodiments, at least a portion of a column may be arranged within a heater, or a column may be arranged outside of fa heater. Alternatively or in addition, a heater may be arranged in series with a column such that a mobile phase passes through the heater before reaching the column. In exemplary embodiments, various sensors, such as temperature sensors, may be provided to monitor the temperature of the mobile phase entering the column and/or exiting the column. In various embodiments, which can be used in conjunction with any of the above aspects and embodiments, the chromatographic systems further comprise a detector. In various embodiments, the outlet of the chromatographic separation device is directly connected to the detector. In some of these embodiments, the chromatographic separation device and detector are provided in a single device. Examples of such a configuration, specifically, a column directly coupled to a mass spectrometer ion source device such as an electrospray ionization emitter, are described in United States Patent Application No. 2019/0317062 to Fogwill et al.

In various embodiments, which can be used in conjunction with any of the above aspects and embodiments, the detector is a fluorescence detector, or a detector based on UV, Visible and/or near IR light, among others.

In various embodiments, which can be used in conjunction with any of the above aspects and embodiments, the detector is a mass spectrometer. In certain of these embodiments, the mass spectrometer is a quadrupole-based mass spectrometer and/or an ion mobility spectrometer and/or a time of flight based mass spectrometer. In certain embodiments, the mass spectrometer may be a quadrupole-based hybrid high resolution mass spectrometer (HRMS) or high resolution ion mobility mass spectrometer (HDMS, high definition mass spectrometer).

In various aspects, the present disclosure provides methods for separating biomolecules comprising: (a) loading an aqueous solution comprising the biomolecules into the inlet of the housing of a chromatographic separation device in accordance with any of the above aspects and embodiments, thereby loading the biomolecules onto the sorbent particles within the internal volume of the housing and (b) introducing a mobile phase selected from an aqueous acidic mobile phase comprising water and a volatile acid or an aqueous basic mobile phase comprising water and a volatile base into the inlet of the chromatographic separation device in a volume sufficient to elute at least a portion of the loaded biomolecules from the sorbent in an eluent stream from the outlet of the housing.

In various embodiments, which can be used in conjunction with any of the above aspects and embodiments, the mobile phase further comprises one or more polar organic solvent. Examples of such solvents may be selected from acetonitrile, acetone, tetrahydrofuran, methylene chloride, ethyl acetate, N,N-dimethylformamide, dimethyl sulfoxide, dimethyl ether, methanol, and combinations thereof.

In various embodiments, which can be used in conjunction with any of the above aspects and embodiments, during a course of elution, a composition of the mobile phase changes. In some of these embodiments, a concentration of water in the mobile phase decreases and a concentration of polar organic solvent in the mobile phase increases during the course of elution.

In various embodiments, which can be used in conjunction with any of the above aspects and embodiments, during a course of elution, a temperature of the mobile phase increases or decreases.

In various embodiments, which can be used in conjunction with any of the above aspects and embodiments, the mobile phase, the chromatographic separation device, or both are heated.

In various embodiments, which can be used in conjunction with any of the above aspects and embodiments, the mobile phase is an acidic aqueous mobile phase that comprises water and a volatile acid. In certain of these embodiments, the biomolecules comprise one or more intact proteins. Examples of volatile acids include organic acids such as formic acid, acetic acid, difluoroacetic acid, trifluoroacetic acid, propionic acid, butyric acid, oxalic acid, malonic acid, succinic acid, maleic acid, glutaric acid, and organic hydroxyacids such as glycolic acid, lactic acid, tartaric acid, malic acid, citric acid, gluconic acid, and blends of the foregoing, among others.

In various embodiments, which can be used in conjunction with any of the above aspects and embodiments, the biomolecules comprise one or more intact proteins. In some of these embodiments, the volume of the sorbent particles ranges from 10 to 100 μL and a linear mass spectrometric detection ($R^2>0.90$) is obtained in a sample having between 0.1 and 100 ng of protein. In some of these embodiments, the volume of the sorbent particles ranges from 1 to 10 μL and a linear mass spectrometric detection ($R^2>0.90$) is obtained in a sample having between 0.01 and 10 ng of protein.

In various embodiments, which can be used in conjunction with any of the above aspects and embodiments, the mobile phase is basic aqueous mobile phase that comprises water and a volatile base. In certain of these embodiments, the biomolecules comprise one or more nucleic acid polymers. Examples of volatile bases include ammonium hydroxide and volatile amines including organic amines such as such as methyl amine, methane diamine, ethyl amine, ethyl diamine, diethylamine, diethanolamine, tromethamine, choline, pyrrolidine, pyrrole, piperazine, or pyridine, among others.

In various embodiments, which can be used in conjunction with any of the above aspects and embodiments, the methods for separating biomolecules further comprise analyzing the eluent stream with a detector.

In various embodiments, the detector is a fluorescence detector.

In various embodiments, the detector is a mass spectrometer.

In various embodiments, the detector is a quadrupole-based mass spectrometer. In some of these embodiments, the quadrupole is used as a mass filter. For example, the quadrupole may be used as a mass filter to filter out ions with m/z values less than 1,000, to filter out ions with m/z values 1,500, or to filter out ions with m/z values less than 1,800 m/z, among other examples.

In various embodiments, which can be used in conjunction with any of the above aspects and embodiments, the methods for separating biomolecules further comprise performing gas phase ion mobility separation on the eluent stream.

In various embodiments, which can be used in conjunction with any of the above aspects and embodiments, the eluent stream comprises or is suspected of comprising a target analyte, and the methods for separating biomolecules further comprise calibrating the mass spectrometer with a lockspray standard. In some embodiments, the lockspray standard is electrosprayed under conditions suitable to produce a lockmass ion having a m/z value that is within +/−50% of a lockmass ion value exhibited by the target analyte. In certain embodiments, the lockspray standard is electrosprayed under conditions suitable to produce a lockmass ion between 1,000 and 10,000 m/z, more particularly, between 2,000 and 4,000 m/z.

Other aspects of the present disclosure pertain to kits comprising chromatographic separation devices that comprise (a) sorbent particles formed from an organic polymer and having width ranging from 0.5 to 100 μm, in accordance with any of the above aspects and embodiments and (b) a housing comprising an inlet, an outlet and an internal volume between the inlet and the outlet, the internal volume being filled with a volume of the sorbent particles that has a length ranging from 2 to 50 mm (e.g., ranging anywhere from 2 mm to 5 mm to 10 mm to 20 mm to 30 mm to 40 mm to 50 mm) and a width ranging from 100 μm to 10 mm (e.g., ranging anywhere from 100 μm 200 μm to 500 μm to 1 mm to 2 mm to 5 mm to 10 mm) or being configured to be filled with a volume of the sorbent particles that has a length ranging from 2 to 50 mm (e.g., ranging anywhere from 2 mm to 5 mm to 10 mm to 20 mm to 30 mm to 40 mm to 50 mm) and a width ranging from 100 μm to 10 mm, wherein a direction of fluid flow from the inlet to the outlet of the housing is along the length of the volume of the sorbent particles (e.g., ranging anywhere from 100 μm 200 μm to 500 μm to 1 mm to 2 mm to 5 mm to 10 mm).

In various embodiments, which can be used in conjunction with any of the above aspects and embodiments, an internal surface of the housing surrounding the volume of the sorbent particles has a water contact angle of less than 60°.

In various embodiments, which can be used in conjunction with any of the above aspects and embodiments, the kits further comprise one or more vials. In some of these embodiments, an internal surface of the one or more vials has a water contact angle of less than 60°. In certain embodiments, the vials comprise an internal surface that comprises an $O_2$-plasma-treated polymer surface, such as $O_2$-plasma-treated polyolefin (e.g., polyolefins such as polyethylene and polypropylene, among others) vials.

Further aspects and embodiments will become apparent to those of skill in the art upon review of the detailed description and claims to follow.

DETAILED DESCRIPTION

Many different types of columns and sorbent particles are available for the chromatographic separation and analysis of proteins. In various embodiments, a column or device exhibiting minimal amounts of secondary interactions may be beneficial. While not limited to theory, it is believed that secondary interactions can negatively affect peak shape and peak recovery during the analysis of low mass loads. If high affinity secondary interaction sites, such as those comprised of both ionic and hydrophobic binding sites, are present, an undesirably high mass of protein may be too strongly adsorbed and peak shape and recovery may suffer. The present inventors have found ways to minimize these effects. A first way is to use sorbent particles formed from organic polymers and a second way is to use no more sorbent particles in a column than is needed to afford sufficient retention and selectivity for resolving target analytes. In various embodiments, it is desirable to employ sorbent particles with a large enough pore size to allow a protein of interest to diffuse through. In various embodiments, sorbent particles formed from organic polymers are selected that are suitable for use at elevated temperatures and acidic conditions, as protein LC-MS is generally run at elevated temperatures using a hydrophobic, acidic mobile phase additive for ion pairing. Organic acids, including formic acid (FA), may be used for bioanalysis of proteins to give high MS sensitivities, though a weaker acid with less resolving power than trifluoroacetic acid (TFA) may be effectively used as well.

Various different sorbent particles have been used for protein bioanalysis. However, the present inventors have found that the performance of these sorbent particles can differ drastically depending on the application and the desired limits of detection. For instance, as indicated above, for very low detection limits, it has been shown that minimizing secondary interactions can be important. Analyses of silica, organo-silica, and polymeric sorbent particles demonstrate that sorbent particles containing silanols can be detrimental to the trace level detection of protein analytes (see Example 1 below). While organosilica shows itself to be a better choice than 100% silica particles, in various embodiments, 100% polymer-based sorbent particles are superior. In some embodiments, the sorbent particles are based on polymers containing styrene, divinylbenzene, methacrylate, methylmethacrylate, or mixtures thereof. These sorbent particles can be non-porous, or can be porous or superficially porous in nature, containing pore diameters ranging from 10 to 5000 Å, beneficially, 100 to 3000 Å. These sorbent particles can also exhibit particle diameters ranging from 1 to 100 μm, more ideally 1.5 to 5 μm.

While not limited to theory, it appears that the number of secondary interactions in a column device is proportional to the amount of stationary phase or the size of a column bed, which in turn effects protein peak shape and recovery across the regime of low mass loads. To demonstrate this, present inventors have compared separations using 2.1 mm ID×5, 10, 15, 20, and 50 mm long column devices (see Example 2 below). From 10 to 50 mm lengths, separation resolving power was seen to be comparable and there was only a noticeable decrease in resolution with the 5 mm device. Accordingly, in certain preferred embodiments, a packed column is used that has an internal diameter dimension of 100 μm to 4.6 mm ID and a length ranging from 5 to 50 mm, more preferably, 10 to 20 mm.

In theory, a sorbent particles having a large pore size coupled with a sufficiently small particle diameter should provide improved separation performance and detection capability. In this regard, the present inventors have found that by investigating the porosity of polymeric polystyrene-divinylbenzene (PS-DVB) particles, a pore size larger than 1000 Å can provide resolution benefits. Moreover, a smaller particle size may also be beneficial. A 3 μm, 2000 Å PS-DVB particle has shown to provide higher peak capacities than a 5 μm, 1000 Å particle and has been shown to demonstrate low limits of detection—down to a 0.025 ng mass load for a neat solution of NIST mAb without the use of a carrier protein—suggesting that these sorbent particles provide a good balance of particle size and pore size for protein bioanalysis (see Example 3 below). In some specific embodiments, a column device having a 10 to 100 μL empty volume chamber is packed with a 1 to 5 μm diameter sorbent particles and is used to achieve linear mass spectrometric detection ($R^2 > 0.90$) between 0.1 and 100 ng of protein. In other embodiments, a column device having a 1 to 10 μL empty volume chamber is packed with a 1 to 5 μm diameter sorbent particles and is used to achieve linear mass spectrometric detection ($R^2 > 0.90$) between 0.01 and 10 ng of protein.

Using a column with a purposefully short bed of sorbent particles, liquid chromatography techniques have also been optimized. For example, column temperature can be used to improve sensitivity and peak shape, enabling faster run times, and eluting analytes such as proteins or other biomolecules. The present inventors have found that a short column with reduced amounts of chromatographic material is more responsive to changes in temperature and can be quicker to arrive at and cool down from elevated temperatures than a longer column or one containing more stationary phase material. By coupling a temperature gradient with a mobile phase composition gradient, enhance selectivity, resolution, and sensitivity of protein analytes can be obtained (sec Example 4). In some embodiments, a set temperature may be coupled with a multi-isocratic mobile phase composition profile, or a temperature gradient may be coupled with a multi-isocratic mobile phase composition profile, or a multi-isocratic temperature profile may be coupled with a constant mobile phase composition, or a multi-isocratic temperature profile may be coupled with a mobile phase composition gradient, or a multi-isocratic temperature profile may be coupled with a multi-isocratic mobile phase composition profile, which may be beneficial in separations involving multiple protein species, for example, those involving carrier proteins.

In other embodiments, using either an isocratic or a thermal gradient, it is shown that by using solely active preheating, or simply heating the mobile phase as it enters the column, can give equivalent or even advantageous selectivity to those separations using a column heater (see Example 5). By avoiding the use of a column heater, one can directly couple the column to a detector inlet using active preheating. In this way, sensitivity can be improved by reducing the tubing leading to the detector and thus minimizing dispersion. Moreover, a short bed length column directly integrated to an MS interface with optimized temperature control may minimize dispersion and increase MS sensitivity even further. Relatedly, direct or integrated coupling of a fluorescence detector to a short bed length column device, with or without optimized temperature control, may also improve FLR sensitivity for viable, sub-nanogram quantitation.

It has also been found that problematic sample loss can occur when monoclonal antibodies and antibody drug conjugates are serially diluted into glass sample vessels. To mitigate these sample losses, $O_2$ plasma treated polypropylene vials may be employed. In turn, lower limits of detection can be obtained along with improved linearity across a wider dynamic range (see Example 3). Polymeric or vapor deposition coated sample vessels, mobile phase flow paths, column hardware and detector components may also enhance analyte recovery.

To accurately detect low concentrations of protein analytes, high sensitivity MS may be used in conjunction with the above-noted column technology and liquid chromatography conditions. In particular, with a quadrupole based hybrid mass spectrometer, an analyst can improve sensitivity by operating the quadrupole as a mass filter selective for only high m/z ions. As such, quadrupole tuning can be extremely useful in optimizing protein detection by HRMS, especially when it is used to achieve low limits of detection. For peptide and protein analyses, a quadrupole time-of-flight mass spectrometer (QTOF MS) may be employed. The quadrupole manages the transmission of ions based on RF and DC voltages applied to its rods, where the motion of the ions can then be characterized by Mathieu's equation. By adjusting these voltages, ions can pass through the quadrupole or collide with the rods, discharging out undetected. This selective filtering of ions can be useful to tune for ions of lower m/z or, alternatively, of higher m/z.

To date, HRMS protein quantitation analyses have been performed with automatic settings for the quadrupole, which gives a full scan and transmission of both low and high m/z ions. However, the present inventors have observed that there is significant advantage to tuning the quadruple of a hybrid instrument so that it transmits only the ions corresponding to the natural charge state distribution of the intact protein analytes of interest. In effect, this has greatly increased mass spectrometric sensitivity and detection. For example, when infusing and detecting an anti-citrinin murine mAb, tuning the quadrupole to transmit only 2,000 to 5,000 m/z ions led to drastically improved signal-to-noise (see Example 6). In turn, this allows for higher sensitivity to be achieved when running LC-MS separations, as the present inventors have shown a two-fold increase in extracted ion chromatogram (XIC) peak areas. In some embodiments, the methods of the present disclosure are thus combined with quadrupole mass filtering that neutralizes and filters out ions with m/z values less than 1,000, beneficially less than 1,500, and more beneficially less than 1,800 m/z.

The present inventors have also investigated complementary gas phase separations and data processing software. With these techniques, a gas phase ion mobility separation can be incorporated that resolves protein conformations and key analytes according to their collisional cross sections and a millisecond timescale separation. When adding ion mobility between the LC separation and MS detection, as can be done with an ion mobility spectrometry capable (IMS)-QTOF mass spectrometer such as the Vion® IMS-QTOF (Waters Corporation, Milford, MA), the selectivity of the separation can be improved utilizing the drift time analysis of the ions. In this regard, the Vion® mass spectrometer is capable of partially resolving trastuzumab and albumin (bovine serum albumin) according to their differences in gas phase ion mobility (see Example 7). The ion mobility resolution of the Vion® is lower than that of other commercially available IMS instruments such as the SYNAPT G2-Si system (Waters Corporation). As such, it is reasonable to assume that the benefits of IMS will become even more apparent with some other types of instrumentation. In some embodiments a cyclic ion mobility separator may be employed, further increasing IMS resolution. In various embodiments, the methods of the present disclosure include the use of an ion mobility separation to either filter out ions with undesirable drift times or to facilitate more thorough data analysis. In this regard, various algorithms can be used to deconvolute charge state distributions into a single uncharged ion peak. Quantitation may then be applied to the deconvoluted data. Alternatively, signals may be quantitated in the form of individual charge states, multiple combined charge states, or extracted ion chromatograms. In general, it is common practice to use the raw data and measure the intensities of or extracted ion chromatograms corresponding to the top charge states of a protein analyte; however, this sacrifices ion signal and selectivity versus noise. Maximum entropy has been a primary example of a processing tool for deconvolution, and other algorithms such as those based on parsimony analysis have also been used. Optimizing the deconvoluted signal processing may produce even more accurate quantitation of proteins.

Mass calibration techniques may also be employed in some embodiments. By running a reference, or lockspray, standard alongside the analyte, accurate mass measurements can be obtained. However, the standards used are normally those that give much lower m/z values than what would be expected from the electrospray of intact proteins. To provide for more accurate calibration, one can use a reference compound with an MS profile in the range of the target analyte. As a result, in the present disclosure, a lockspray compound and electrospray conditions have been specifically selected to give a more suitable lockspray signal. In one embodiment, the present inventors chose the Enolase T37 peptide as the lockspray standard due to its molecular weight of 2827.3 g/mol, which would give 2828.3 m/z at a +1 charge state. Other compounds containing values within the m/z window of interest are also contemplated, including but not limited to melittin, ubiquitin and insulin. With Enolase T37, it was optimal to electrospray the peptide at a dilute concentration from a mixture of 10 mM ammonium acetate with 0.2% ammonium hydroxide. In Example 8, optimized quadruple settings were also used to increase sensitivity for the 1+ charge state ion. Modifying the desolvation gas flow using vapor from an acid or base such as triethylamine may also further optimize the 1+ charge state ion and even provide charge state reduction advantages to the MS quality of biomolecules. In some embodiments, a lockspray compound is electrosprayed under suitable conditions to produce a lockmass ion between 2,000 and 4,000 m/z. In some embodiments, the electrospray may be interchanged with the effluent of the column device, for example, using a baffle, such that more accurate real time mass correction can be achieved.

With the optimization of column device, liquid chromatography gradient conditions, mass spectrometer approaches, and/or processing algorithms, the present disclosure provides a detailed method that can be used for the quantitative analysis of proteins using LC-MS. A device with a purposely small bed volume may be paired with a wide-pore, polymeric stationary phase in order to improve protein recovery, provide high throughput capabilities, and better peak shape across a wider dynamic range of mass loading. Coupled with quadruple and lockspray tuning, higher MS sensitivity, lower limits of detection, and more reliable peak picking can be achieved. In further embodiments, these devices may be used for separation of other biomolecules such as nucleic acid polymers, for separation and analysis of small molecules, in which case smaller pore diameter sorbent particles may be employed, or may be used for other applications, such as for protein titer analysis, protein desalting, multidimensional analyses, among other applications.

Example 1. Protein Recovery with Different Sorbent Particles

Figure 1:
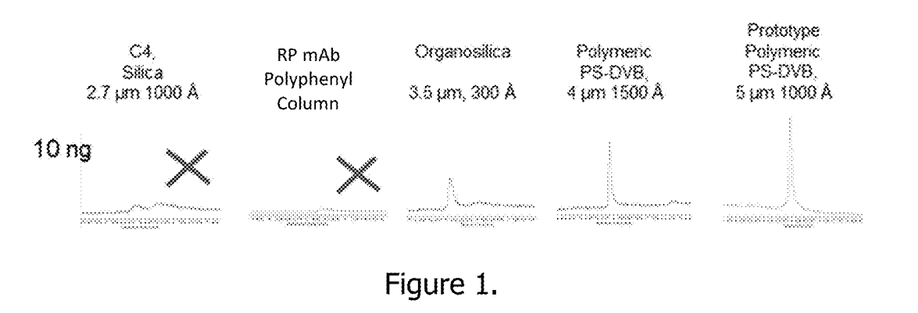
FIG. 1 presents chromatographic separation data obtained of anti-citrinin murine mAb protein recovery across different stationary phases as observed using a 2.1×50 mm column.

Anti-citrinin murine mAb was obtained in the form of the Waters Intact mAb Mass Check Standard. The contents of the vials were reconstituted in 0.1% (w/v) formic acid in water, and serial dilutions were performed using the same sample diluent. Analyses of this sample were performed using a Waters Corporation ACQUITY UPLC H-Class Bio LC system and the separation method outlined below. FIG. 1 presents chromatographic data obtained with various RPLC columns.

LC Conditions
  Columns: Superficially porous C4, 1000 Å 2.7 μm, 2.1×
    50 mm

Superficially porous, 450 Å 2.7 μm Polyphenyl BioResolve™ RP mAb Polyphenyl Column), 2.1×50 mm
Organosilica 300 Å 3.5 μm (Waters BEH (Ethylene Bridged Hybrid) Technology™), 2.1×50 mm
Polymeric PS-DVB 1500 Å 4 μm, 2.1×50 mm
Polymeric PS-DVB 1000 Å 5 μm, 2.1×50 mm
Mobile Phase A: 0.1% (w/v) formic acid in water
Mobile Phase B: 0.1% (w/v) formic acid in acetonitrile
Column Temperature: 80° C.
Injection Volume: 0.5 μL
Sample Concentration: 0.02 μg/μL
Sample Diluent: 0.1% (w/v) formic acid in water
FLR Detection: Ex 280 nm (10 Hz), Em 320 nm Gradient Table:

| Time(min) | Flow Rate(mL/min) | % A | % B | Curve |
|---|---|---|---|---|
| Initial | 0.200 | 85.0 | 15.0 | Initial |
| 10.00 | 0.200 | 45.0 | 55.0 | 6 |
| 10.15 | 0.200 | 20.0 | 80.0 | 6 |
| 10.65 | 0.200 | 20.0 | 80.0 | 6 |
| 10.80 | 0.200 | 85.0 | 15.0 | 6 |
| 12.50 | 0.200 | 85.0 | 15.0 | 6 |

Example 2. Peak Capacity with Varying Column Lengths

Figure 2:
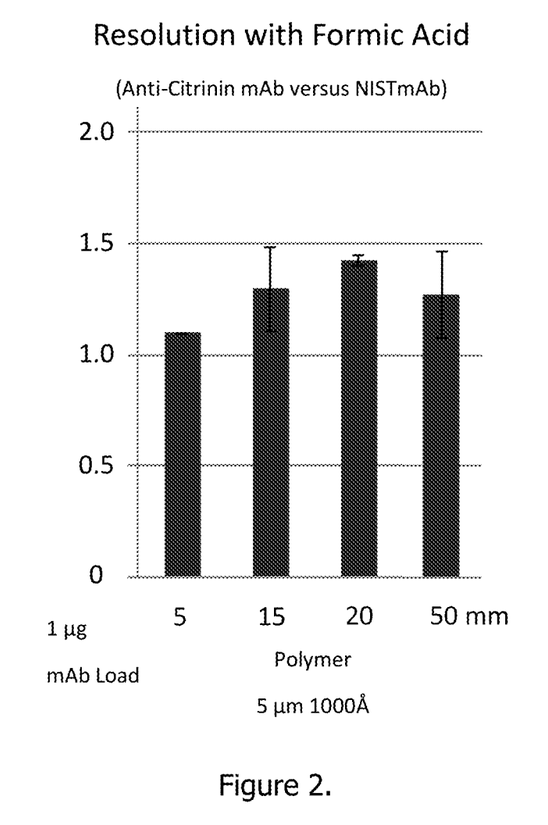
FIG. 2 presents effective peak capacity values for anti-citrinin murine mAb versus NIST mAb as observed using different length columns of a poly(styrene-co-divinyl benzene) (PS-DVB) stationary phase.
Figure 3A:
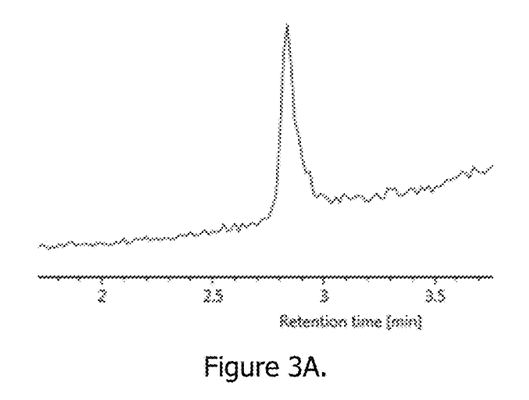
FIGS. 3A-3D illustrate the broad dynamic detection range of the 2.1×15 mm PS DVB column as shown through an extracted ion chromatogram (XIC) (FIG. 3A), MS data from sub nanogram detection of NIST Reference Material 8671 (FIG. 3B, raw MS data, FIG. 3C, deconvoluted MS data) as well as a calibration curve plotting the mass loads of NIST mAb from 0.025 ng to 200 ng (FIG. 3D).
Figure 3B:
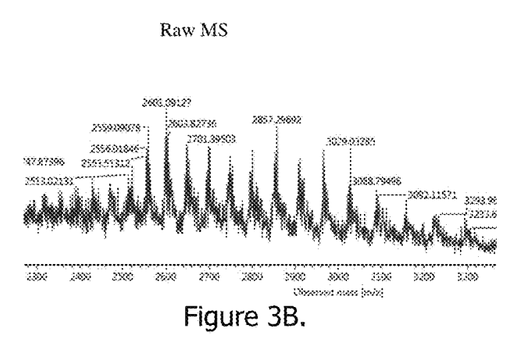
Figure 3C:
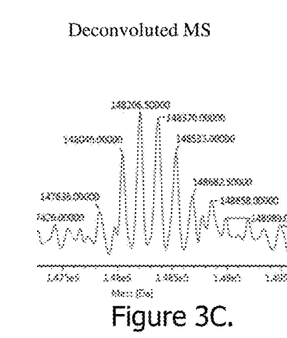
Figure 3D:
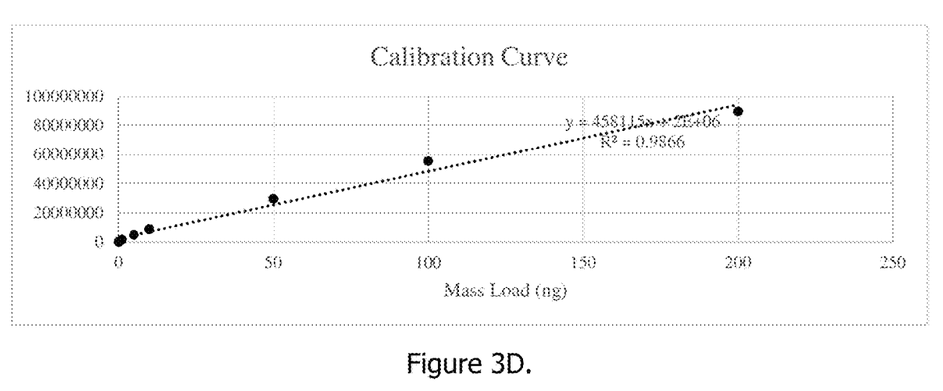

Anti-citrinin murine mAb was obtained in the form of the Waters Corporation Intact mAb Mass Check Standard. NIST mAb was obtained in the form of Waters Corporation Humanized mAb Mass Check Standard. The contents of the vials were reconstituted in 0.1% (w/v) formic acid in water. Analyses of these samples were performed using a Waters Corporation ACQUITY UPLC H-Class Bio LC system and the separation method outlined below. FIG. 2 presents the resolution of the separations as obtained with various length columns of a polymeric PS-DVB stationary phase.
LC Conditions
Columns: Polymeric PS-DVB 1000 Å 5 μm, 2.1×5 mm
Polymeric PS-DVB 1000 Å 5 μm, 2.1×15 mm
Polymeric PS-DVB 1000 Å 5 μm, 2.1×20 mm
Polymeric PS-DVB 1000 Å 5 μm, 2.1×50 mm
Mobile Phase A: 0.1% (w/v) formic acid in water
Mobile Phase B: 0.1% (w/v) formic acid in acetonitrile
Column Temperature: 90° C.
Injection Volume: 0.5 or 2 μL
Sample Concentration: 0.5 or 2 μg/μL
Sample Diluent: 0.1% (w/v) formic acid in water
FLR Detection: Ex 280 nm (10 Hz), Em 320 nm Gradient Table:

| Time(min) | Flow Rate(mL/min) | % A | % B | Curve |
|---|---|---|---|---|
| Initial | 0.200 | 85.0 | 15.0 | Initial |
| 5.00 | 0.200 | 45.0 | 55.0 | 6 |
| 5.07 | 0.200 | 20.0 | 80.0 | 6 |
| 5.32 | 0.200 | 20.0 | 80.0 | 6 |
| 5.40 | 0.200 | 85.0 | 15.0 | 6 |
| 6.25 | 0.200 | 85.0 | 15.0 | 6 |

Example 3. MS with Dynamic Detection Range

NIST mAb was obtained in the form of Waters Corporation Humanized mAb Mass Check Standard and reconstituted in 0.1% (w/v) formic acid in water. Serial dilutions were performed using the same sample diluent. Analyses of these samples were performed using a Waters Corporation ACQUITY UPLC H-Class Bio LC system and Vion® IMS-QTOF mass spectrometer and the separation method outlined below. FIGS. 3A-3D presents the dynamic range of the separations as obtained with a short, prototype polymeric PS-DVB stationary phase.
LC Conditions
Columns: Polymeric PS-DVB 2000 Å 3 μm, 2.1×15 mm
Mobile Phase A: 0.1% (w/v) formic acid in water
Mobile Phase B: 0.1% (w/v) formic acid in acetonitrile
Column Temperature: 90° C.
Injection Volume: 1 μL
Sample Concentration: 0.000025 to 0.2 μg/μL
Sample Diluent: 0.1% (w/v) formic acid in water Gradient Table:

| Time(min) | Flow Rate(mL/min) | % A | % B | Curve |
|---|---|---|---|---|
| Initial | 0.200 | 85.0 | 15.0 | Initial |
| 5.00 | 0.200 | 45.0 | 55.0 | 6 |
| 5.07 | 0.200 | 20.0 | 80.0 | 6 |
| 5.32 | 0.200 | 20.0 | 80.0 | 6 |
| 5.40 | 0.200 | 85.0 | 15.0 | 6 |
| 6.25 | 0.200 | 85.0 | 15.0 | 6 |

MS Conditions
Mode: ESI positive, sensitivity
Mass Range: 2000-4000 m/z
Capillary: 2.25 kV
Sampling Cone: 140 V
Source Offset: 140 V
Source Temperature: 150° C.
Desolvation Temperature: 600° C.
Desolvation Gas: 600 L/h
Collision Energy: 6V
Quadrupole Option: Automatic or Manual
Manual Profile m/z: 2000, 2750, 3500

Example 4. Thermal Gradient

Figure 4A:
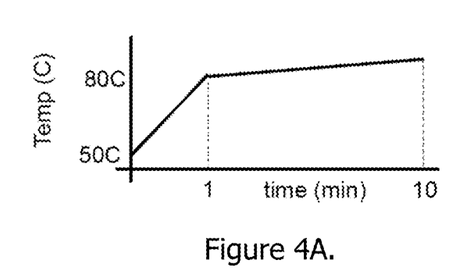
FIGS. 4A-4C represents data collected using a thermal gradient coupled with an elution gradient as obtained with a sub 1 mm ID, 5 cm length column device, using a thermal gradient (FIG. 4A) and an elution gradient (FIG. 4B) for a 1 ng mass load detection and separation of trastuzumab using BSA as a carrier protein (FIG. 4C).
Figure 4B:
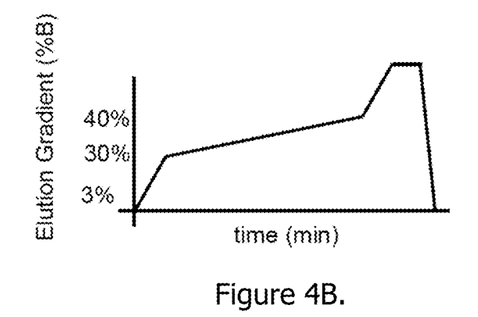
Figure 4C:
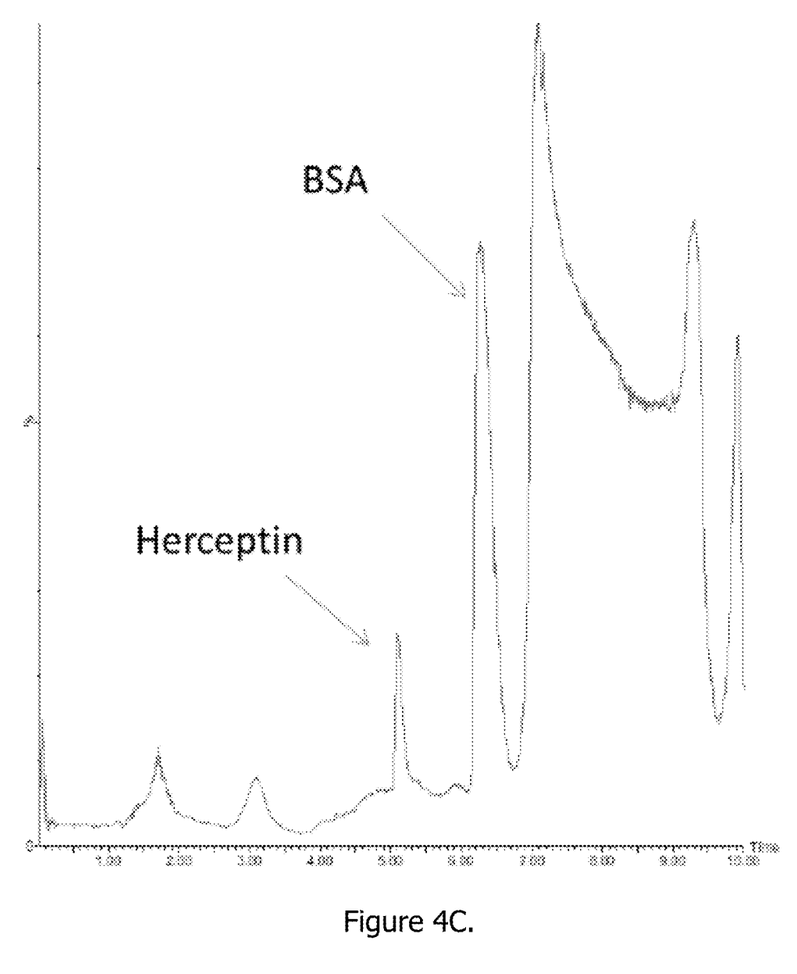
Figure 5A:
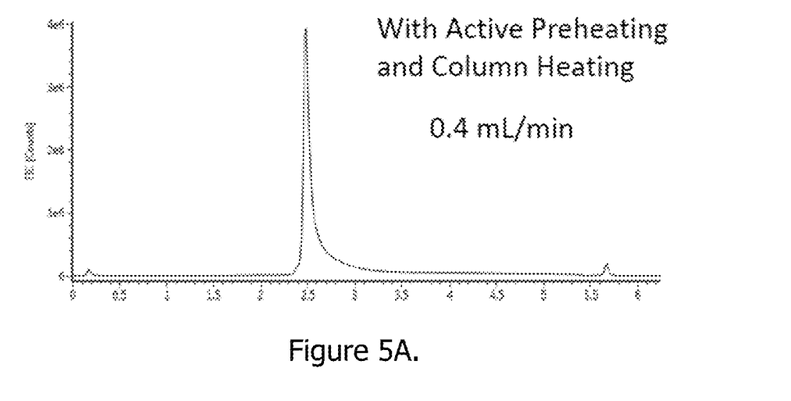
FIGS. 5A-5B show LC MS chromatographic selectivity comparison for a 100 ng mass load separation of anti-citrinin murine mAb using 2.1×15 mm PS DVB column with active preheating and column heating (FIG. 5A) and with active preheating but without column heating (FIG. 5B).
Figure 5B:
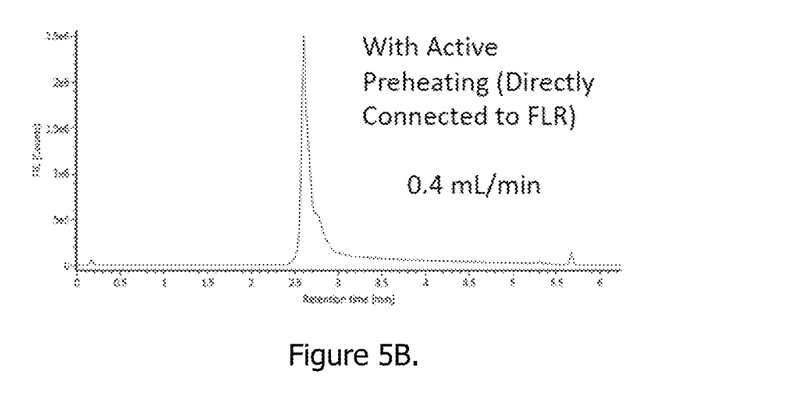

Trastuzumab was spiked to rat plasma and immunoprecipitated using Protein A. Trastuzumab was released from the antibody and BSA was added at concentration of 0.1 mg/mL. FIG. 4 represents data collected using a thermal gradient coupled with an elution gradient as obtained with a sub 1 mm ID, 5 cm length column device.
LC Conditions
Columns: Hybrid Silica C18, 300 Å 1.7 μm, sub 1 mm×5 cm
Mobile Phase A: 0.1% (w/v) formic acid in water
Mobile Phase B: 0.1% (w/v) formic acid in acetonitrile
Column Temperature: 90° C.
Injection Volume: 1 μL
Sample Concentration: 10 ng/μL
Sample Diluent: 0.1% (w/v) formic acid in water
Analytical Flow Rate: 5 μL/min
MS Conditions
Mode: ESI positive, sensitivity
Mass Range: 500-4000 m/z
Capillary: 3.5 kV
Sampling Cone: 190 V
Source Offset: 150 V
Source Temperature: 150° C.
Nanoflow Gas: 0.10 bar, constant pressure Collision Energy: Off
Quadrupole Option: Automatic Example 5. MS with Direct Column Connection Anti-citrinin murine mAb was obtained in the form of the Waters Corporation Intact mAb Mass Check Standard. The contents of the vials were reconstituted in 0.1% (w/v) formic acid in water. Analyses were performed using a Waters Corporation ACQUITY UPLC H-Class Bio LC system and the separation method outlined below. FIG. 5 presents the resolution of the separations as obtained with a short, prototype polymeric PS-DVB stationary phase using active preheating alongside column heating and active preheating only.

LC Conditions
　Columns: Polymeric PS-DVB 1000 Å 5 μm, 2.1×15 mm
　Mobile Phase A: 0.1% (w/v) formic acid in water
　Mobile Phase B: 0.1% (w/v) formic acid in acetonitrile
　Column Temperature: 90° C.
　Injection Volume: 1 μL
　Sample Concentration: 0.1 μg/μL
　Sample Diluent: 0.1% (w/v) formic acid in water

| Gradient Table: | | | | |
|---|---|---|---|---|
| Time(min) | Flow Rate(mL/min) | % A | % B | Curve |
| Initial | 0.200 | 85.0 | 15.0 | Initial |
| 5.00 | 0.200 | 45.0 | 55.0 | 6 |
| 5.07 | 0.200 | 20.0 | 80.0 | 6 |
| 5.32 | 0.200 | 20.0 | 80.0 | 6 |
| 5.40 | 0.200 | 85.0 | 15.0 | 6 |
| 6.25 | 0.200 | 85.0 | 15.0 | 6 |

MS Conditions
　Mode: ESI positive, sensitivity
　Mass Range: 2000-4000 m/z
　Capillary: 2.25 kV
　Sampling Cone: 140 V
　Source Offset: 140 V
　Source Temperature: 150° C.
　Desolvation Temperature: 600° C.
　Desolvation Gas: 600 L/h
　Collision Energy: 6 V
　Quadrupole Option: Automatic or Manual
　Manual Profile m/z: 2000, 2750, 3500

Example 6. MS with Quadruple Tuning

Figure 6A:
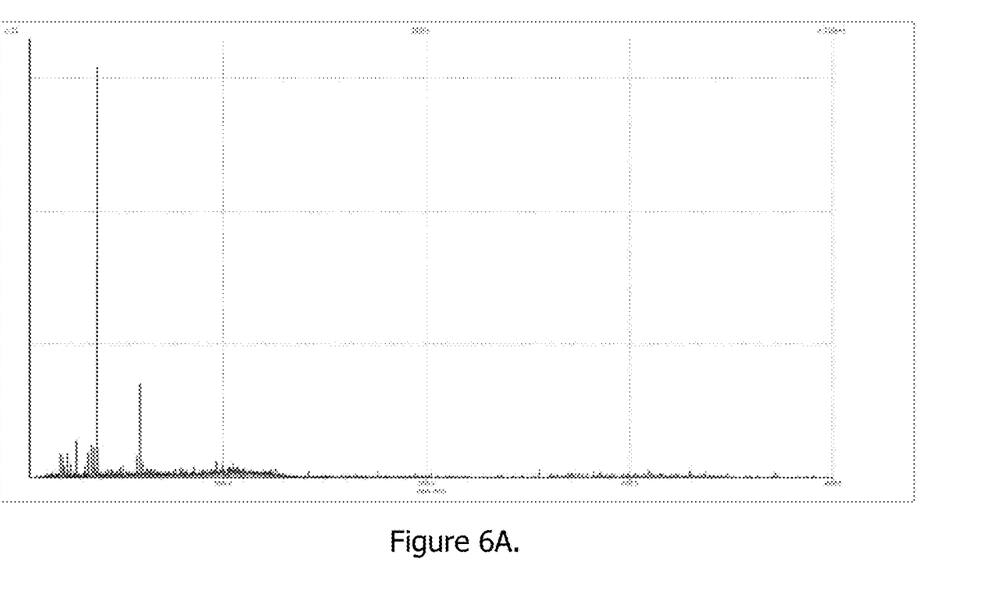
FIGS. 6A-6B present a mass spectrometric comparison as detected through the infusion of an anti-citrinin mAb using a Vion® IMS QToF mass spectrometer using automatic profile (FIG. 6A) and manual profile quadrupole (FIG. 6B) settings.
Figure 6B:
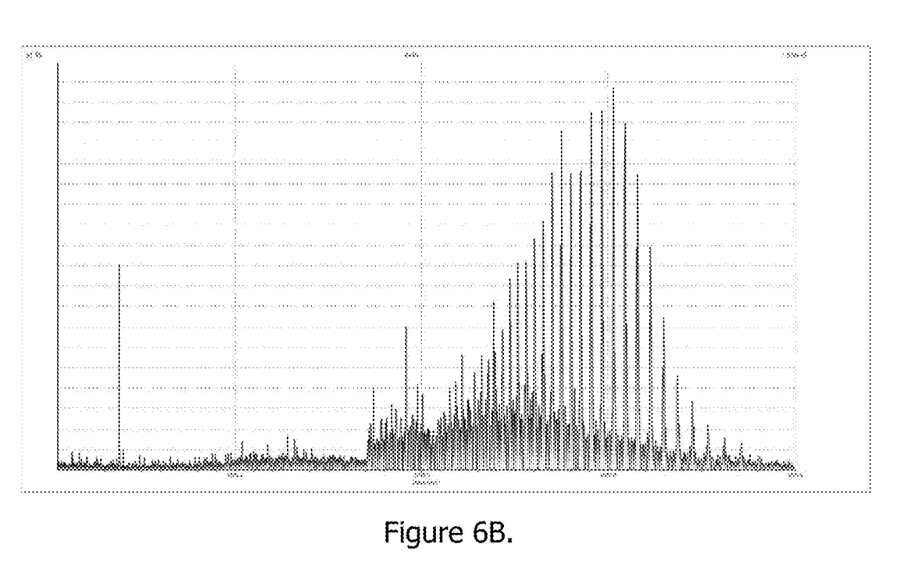

Anti-citrinin murine mAb was obtained in the form of the Waters Corporation Intact mAb Mass Check Standard and purified via Protein A to give a 2.5 mg/mL solution in 10 mM ammonium acetate. The sample was diluted to 0.1 mg/mL with water and infused into the Vion® IMS-QTOF mass spectrometer using the MS settings outlined below. FIG. 6 presents the mass spectrometric comparison obtained using the automatic and manual quadrupole options under the MS profiles.

MS Conditions
　Mode: ESI positive, sensitivity
　Mass Range: 2000-4000 m/z
　Capillary: 2.25 kV
　Sampling Cone: 140 V
　Source Offset: 140 V
　Source Temperature: 150° ° C.
　Desolvation Temperature: 600° C.
　Desolvation Gas: 600 L/h
　Collision Energy: 6 V
　Infusion Flow Rate: 20.00 ML/min
　Quadrupole Option: Automatic or Manual
　Manual Profile m/z: 2000, 2750, 3500

Example 7. MS with Ion Mobility

Figure 7A:
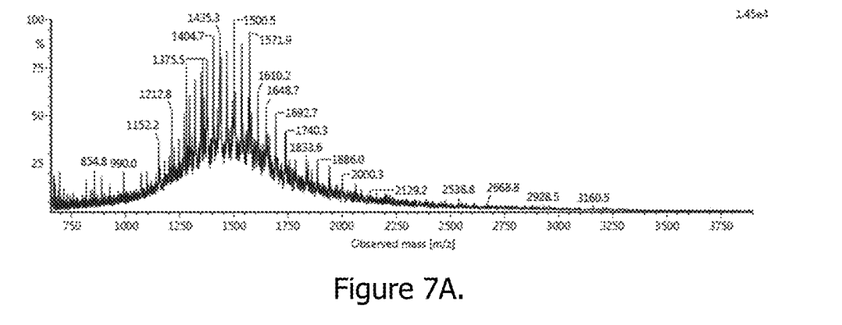
FIGS. 7A-7C represents ion mobility spectra comparison for a coeluting mixture of trastuzumab (25 ng mass load) and bovine serum albumin. Mass spectra of trastuzumab is shown before IMS extraction through full scan (FIG. 7A) and zoomed spectra (FIG. 7B) and after IMS extraction with a zoomed spectrum (FIG. 7C).
Figure 7B:
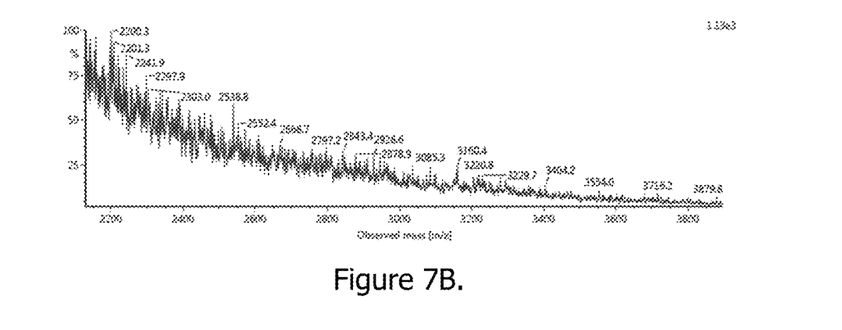
Figure 7C:
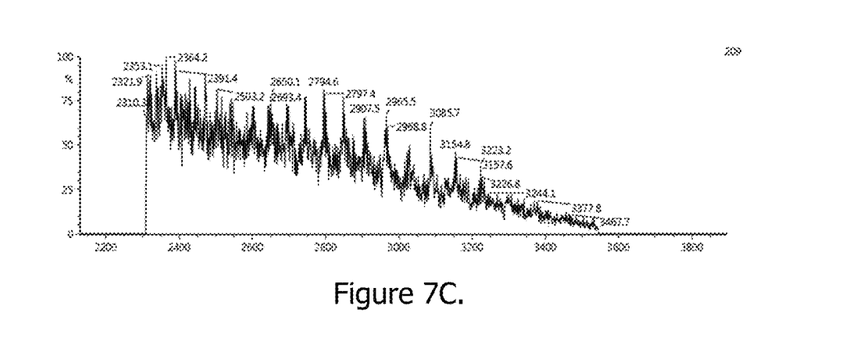

Trastuzumab spiked to mouse plasma at 5 μg/mL was immunopurified using goat anti-human Fc capturing antibody. Trastuzumab was released from the antibody using 0.1% TFA and BSA was added at concentration of 0.1 mg/mL. FIG. 7 represents comparison of data collected with and without ion mobility in data acquisition.

LC Conditions
　Columns: Polymeric PS-DVB 1500 Å 4 μm, 2.1×50 mm
　Mobile Phase A: 0.1% (w/v) formic acid in water
　Mobile Phase B: 0.1% (w/v) formic acid in acetonitrile
　Column Temperature: 80° C.
　Injection Volume: 1 μL
　Sample Concentration: 5 μg/mL
　Sample Diluent: 0.1% (w/v) formic acid in water

| Gradient Table: | | | | |
|---|---|---|---|---|
| Time(min) | Flow Rate(mL/min) | % A | % B | Curve |
| Initial | 0.200 | 95.0 | 5.0 | Initial |
| 2.00 | 0.200 | 30.0 | 70.0 | 6 |
| 2.50 | 0.200 | 10.0 | 90.0 | 6 |
| 3.00 | 0.200 | 10.0 | 90.0 | 6 |
| 3.50 | 0.200 | 95.0 | 5.0 | 6 |
| 8.00 | 0.200 | 95.0 | 5.0 | 6 |

Figure 8:
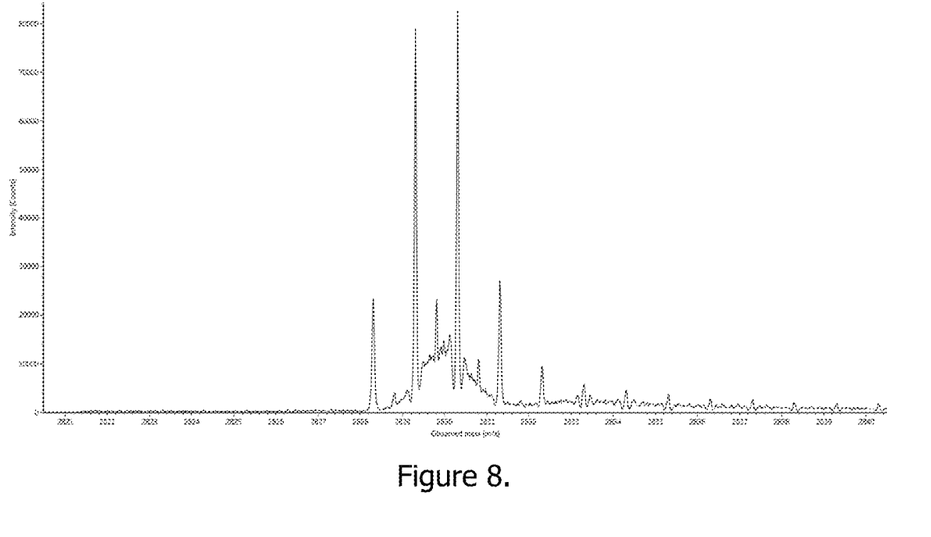
FIG. 8 presents the mass spectra of enolase T37 obtained from the total ion chromatogram of the lockspray channel while running a separation of anti-citrinin murine mAb.

MS Conditions
　Mode: ESI positive, sensitivity
　Mass Range: 500-4000 m/z
　Capillary: 2.75 kV
　Sampling Cone: 140 V
　Source Offset: 140 V
　Source Temperature: 150° C.
　Desolvation Temperature: 600° C.
　Desolvation Gas: 800 L/h
　Collision Energy: 6 V
　Quadrupole Profile Option: Automatic Example 8. MS with Targeted Lockspray Enolase T37 peptide was obtained from New England BioLabs (Ipswich, MA) and reconstituted in 50:50 water:acetonitrile modified with 0.1% formic acid. The sample was diluted to 0.1 mg/mL with 10 mM ammonium acetate modified with 0.2% ammonium hydroxide and infused as the lockspay reference standard for separations of an anti-citrinin murine mAb using the method and a Waters Corporation ACQUITY UPLC H-Class Bio LC system and Vion® IMS-QTOF mass spectrometer as outlined below. The anti-citrinin murine mAb was obtained in the form of the Waters Corporation Intact mAb Mass Check Standard and reconstituted in 0.1% (w/v) formic acid in water. FIG. 8 presents the mass spectra of enolase T37 obtained from the total ion chromatogram of the lockspray channel while running a separation of anti-citrinin murine mAb.

LC Conditions
　Columns: Polymeric PS-DVB 2000 Å 3 μm, 2.1×15 mm
　Mobile Phase A: 0.1% (w/v) formic acid in water
　Mobile Phase B: 0.1% (w/v) formic acid in acetonitrile Column Temperature: 90° C.
Injection Volume: 1 µL
Sample Concentration: 0.005 µg/µL
Sample Diluent: 0.1% (w/v) formic acid in water

| Gradient Table: | | | | |
|---|---|---|---|---|
| Time(min) | Flow Rate(mL/min) | % A | % B | Curve |
| Initial | 0.200 | 85.0 | 15.0 | Initial |
| 5.00 | 0.200 | 45.0 | 55.0 | 6 |
| 5.07 | 0.200 | 20.0 | 80.0 | 6 |
| 5.32 | 0.200 | 20.0 | 80.0 | 6 |
| 5.40 | 0.200 | 85.0 | 15.0 | 6 |
| 6.25 | 0.200 | 85.0 | 15.0 | 6 |

MS Conditions
  Mode: ESI positive, sensitivity
  Mass Range: 2000-4000 m/z
  Capillary: 2.25 kV
  Sampling Conc: 140 V
  Source Offset: 140 V
  Source Temperature: 150° C.
  Desolvation Temperature: 600° C.
  Desolvation Gas: 600 L/h
  Collision Energy: 6 V
  Infusion Flow Rate: 20.00 L/min
  Reference Capillary: 2.25 kV
  Quadrupole Option: Automatic or Manual
  Manual Profile m/z: 2000, 2750, 3500

The invention claimed is:

1. A method for separating and analyzing one or more intact proteins comprising:
   introducing a sample comprising the one or more intact proteins into an inlet of a chromatographic separation device that comprises
   (a) sorbent particles formed from an organic polymer formed from one or more monofunctional or multifunctional aromatic monomers and having width ranging from 0.5 to 100 m and
   (b) the chromatographic separation device comprising the inlet, an outlet and an internal volume between the inlet and the outlet, the internal volume being filled with a volume of the sorbent particles, wherein the internal volume has a length ranging from 2 to 50 mm and a width ranging from 50 m to 10 mm, wherein a direction of fluid flow from the inlet to the outlet is along the length of the volume of the sorbent particles, and wherein a ratio of the length to the width of the volume of the sorbent particles ranges from 10:1 to 2:1,
   thereby loading the one or more intact proteins onto the sorbent particles; and introducing an acidic mobile phase comprising formic acid, acetic acid and/or a fluorinated carboxylic acid into the inlet of the chromatographic separation device in a volume sufficient to elute at least a portion of the loaded one or more intact proteins from the sorbent particles in an eluent stream from the outlet of the chromatographic separation device; and
   analyzing the eluent stream with a mass spectrometer, wherein the mass spectrometer is calibrated with a lockspray standard electrosprayed under conditions which produce a lockmass ion between 2,000 and 4,000 m/z.

2. The method of claim 1, wherein the one or more monofunctional or multifunctional aromatic monomers comprise styrene and divinyl benzene.

3. The method of claim 1, wherein the sorbent particles are porous particles or superficially porous particles having pore diameters ranging from 300 Å to 5000 Å.

4. The method of claim 1, wherein an internal surface of the internal volume has a water contact angle of less than 60°.

5. The method of claim 1, wherein the mobile phase further comprises one or more polar organic solvents.

6. The method of claim 1, wherein during a course of elution, a composition of the mobile phase changes.

7. The method of claim 1, wherein the mobile phase further comprises one or more polar organic solvents and water.

8. The method of claim 7, wherein a concentration of the water in the mobile phase decreases and a concentration of the polar organic solvent in the mobile phase increases during a course of elution.

9. The method of claim 1, wherein during a course of elution, a temperature of the mobile phase increases.

10. The method of claim 1, wherein during the course of elution, (a) a constant temperature profile is coupled with a multi-isocratic mobile phase composition profile, (b) temperature gradient is coupled with a multi-isocratic mobile phase composition profile, (c) a multi-isocratic temperature profile is coupled with a constant mobile phase composition, (d) a multi-isocratic temperature profile is coupled with a mobile phase composition gradient, or (e) a multi-isocratic temperature profile is coupled with a multi-isocratic mobile phase composition profile.

11. The method of claim 1, wherein the mass spectrometer is a quadrupole-based mass spectrometer and wherein the quadrupole is used as a mass filter.

12. The method of claim 11, wherein the quadrupole is used to filter out ions with m/z values less than 1,000.

13. The method of claim 1, wherein the volume of the sorbent particles ranges from 10 to 100 µL, and a linear mass spectrometric detection ($R^2>0.90$) is obtained in an injected sample having between 0.1 and 100 ng of the one or more intact proteins, or wherein the volume of the sorbent particles ranges from 1 to 10 µL, and a linear mass spectrometric detection ($R^2>0.90$) is obtained in an injected sample having between 0.01 and 10 ng of the one or more intact proteins.

* * * * *